United States Patent [19]

Petersen et al.

[11] Patent Number: 4,703,047

[45] Date of Patent: Oct. 27, 1987

[54] 1-CYCLOPROPYL-1,4-DIHYDRO-4-OXO-7-(4-(2-OXO-1,3-DIOXOL-4-YL-METHYL)-1-PIPERAZINYL)-3-QUINOLINECARBOXYLIC ACID ANTIBACTERIAL AGENTS

[75] Inventors: Uwe Petersen, Leverkusen; Klaus Grohe, Odenthal; Hans-Joachim Zeiler, Velbert; Karl G. Metzger, Wuppertal, all of Fed. Rep. of Germany

[73] Assignee: Bayer Aktiengesellschaft, Leverkusen, Fed. Rep. of Germany

[21] Appl. No.: 822,714

[22] Filed: Jan. 27, 1986

[30] Foreign Application Priority Data

Feb. 12, 1985 [DE] Fed. Rep. of Germany ....... 3504643

[51] Int. Cl.[4] .................. A61K 31/495; C07D 405/14
[52] U.S. Cl. .................................. 514/254; 544/363; 546/156
[58] Field of Search ...................... 544/363; 514/254

[56] References Cited

U.S. PATENT DOCUMENTS

| | | | |
|---|---|---|---|
| 3,849,421 | 11/1974 | Nakagome et al. | 546/123 |
| 4,429,127 | 1/1984 | Irikura et al. | 544/363 |
| 4,455,310 | 6/1984 | Sakamoto et al. | 544/363 |
| 4,472,579 | 9/1984 | Irikura et al. | 544/363 |

FOREIGN PATENT DOCUMENTS

| | | |
|---|---|---|
| 0067411 | 12/1982 | European Pat. Off. |
| 0113091 | 7/1984 | European Pat. Off. |
| 0117474 | 9/1984 | European Pat. Off. |
| 0126355 | 11/1984 | European Pat. Off. |

OTHER PUBLICATIONS

Wise, et al., "Antimicrobial Agents and Chemotherapy", vol. 23(4), 1983, pp. 559-564.

*Primary Examiner*—Glennon H. Hollrah
*Assistant Examiner*—James H. Turnipseed
*Attorney, Agent, or Firm*—Sprung Horn Kramer & Woods

[57] ABSTRACT

Novel antibacterially active 1-cyclopropyl-1,4-dihydro-4-oxo-7-[4-(2-oxo-1,3-dioxol-4-yl-methyl)-1-piperazinyl]-3-quinolinecarboxyic acids of the formula in which $R$ is hydrogen or, together with $R^1$, forms an alkylene radical with 2 or 3 carbon atoms, $R^1$ is hydrogen, alkyl with 1 to 4 carbon atom or phenyl, $R^2$ and $R^3$ each independently is hydrogen, methyl, ethyl, cyclohexyl, methylene-dioxphenyl, furyl, tetrahydrofuryl or thienyl; or phenyl which is optionally mono-, di or tri-substituted by fluorine, chlorine, bromine, methyl, phenyl, cyano, hydroxyl, ethoxy, benzyloxy, amino, methylamino, dimethylamino, piperidino or nitro, $X^1$ is hydrogen, halogen, or nitro, and $X^2$ is hydrogen or halogen, or pharmaceutically acceptable hydrates, acid addition salts, alkali metal salts or alkaline earth metal salts thereof.

12 Claims, No Drawings

1-CYCLOPROPYL-1,4-DIHYDRO-4-OXO-7-(4-(2-OXO-1,3-DIOXOL-4-YL-METHYL)-1-PIPERAZINYL)-3-QUINOLINECARBOXYLIC ACID ANTIBACTERIAL AGENTS

The invention relates to novel 1-cyclopropyl-1,4-dihydro-4-oxo-7-[4-(2-oxo-1,3-dioxol-4-yl-methyl)-1-piperazinyl]-3-quinolinecarboxylic acids, a process for their preparation and antibacterial agents containing these compounds.

It has already been disclosed that 1-ethyl-6-fluoro-1,4-dihydro-4-oxo-7-[4-(5-methyl-2-oxo-1,3-dioxol-4-yl-methyl)-1-piperazinyl]-3-quinolinecarboxylic acid (European Patent Application No. 67,411) and 7-[4-(5-tert.-butyl-2-oxo-1,3-dioxol-4-yl-methyl)-1-piperazinyl]-1-ethyl-6-fluoro-1,4-dihydro-4-oxo-3-quinolinecarboxylic acid (Japanese Patent Application No. 58 069,880) and acid addition salts thereof can be used as antimicrobial active compounds.

It has now been found that the new 1-cyclopropyl-1,4-dihydro-4-oxo-7-[4-(2-oxo-1,3-dioxol-4-yl-methyl)-1-piperazinyl]-3-quinolinecarboxylic acids of the formula (I)

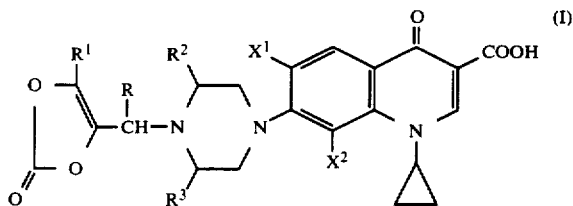

in which
R represents hydrogen or, together with $R^1$, forms an alkylene radical with 2 or 3 carbon atoms,
$R^1$ represents hydrogen, alkyl with 1 to 4 carbon atoms or phenyl,
$R^2$ and $R^3$ can be identical or different and represent hydrogen, methyl, ethyl, cyclohexyl, methylenedioxyphenyl, furyl, tetrahydrofuryl or thienyl, or represent phenyl which is optionally mono-, di- or tri-substituted by fluorine, chlorine, bromine, methyl, phenyl, cyano, hydroxy, methoxy, benzyloxy, amino, methylamino, dimethylamino, piperidino or nitro,
$X^1$ represents hydrogen, halogen, such as fluorine, chlorine or bromine, or nitro and
$X^2$ represents hydrogen or halogen, such as fluorine, chlorine or bromine,
and pharmaceutically usable hydrates, acid addition salts and alkali metal and alkaline earth metal salts thereof, have a powerful antibacterial action.

Preferred compounds of the formula (I) are those in which
R represents hydrogen,
$R^1$ represents methyl ot tert.-butyl,
$R^2$ and $R^3$ can be identical or different and represent hydrogen, methyl, ethyl, cyclohexyl or thienyl, or represent phenyl which is optionally mono-, di- or tri-substituted by fluorine, chlorine, bromine, methyl, phenyl, cyano, hydroxyl, methoxy, amino, piperidino or nitro,
$X^1$ represents hydrogen, halogen, such as fluorine, chlorine or bromine, or nitro and
$X^2$ represents hydrogen or halogen, such as fluorine, chlorine or bromine.

Particularly preferred compounds of the formula (I) are those in which
R represents hydrogen,
$R^1$ represents methyl,
$R^2$ and $R^3$ can be identical or different and represent hydrogen, methyl, cyclohexyl or thienyl, or represent phenyl which is optionally mono- or di-substituted by fluorine, chlorine, bromine, methyl, hydroxyl, methoxy, benzyloxy, amino, piperidino or nitro,
$X^1$ represents halogen, such as fluorine, chlorine or bromine, and
$X^2$ represents hydrogen or halogen, such as fluorine, chlorine or bromine.

It has furthermore been found that the compounds of the formula (I) are obtained by a process in which 1-cyclopropyl-1,4-dihydro-4-oxo-7-(1-piperazinyl)-3-quinolinecarboxylic acids of the formula (II)

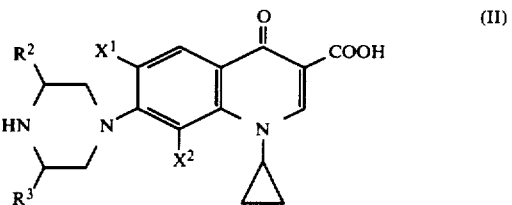

in which
$R^2$, $R^3$, $X^1$ and $X^2$ have the abovementioned meaning, are reacted with compounds of the formula (III)

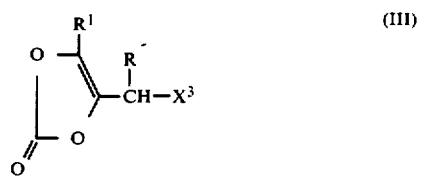

in which
$R^1$ and R have the abovementioned meaning and
$X^3$ represents halogen, such as, for example, chlorine, bromine or iodine, or a radical $O-SO_2-R^4$, wherein
$R^4$ denotes methyl, trifluoromethyl, phenyl or 4-methylphenyl,
if appropriate in the presence of acid-binding agents.

If, for example, 1-cyclopropyl-6-fluoro-1,4-dihydro-4-oxo-7-(1-piperazinyl)-3-quinolinecarboxylic acid and 4-bromomethyl-5-methyl-1,3-dioxol-2-one are used as starting compounds in the reaction according to the invention, the course of the reaction can be represented by the following equation:

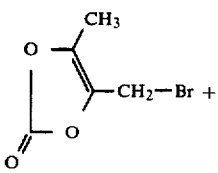

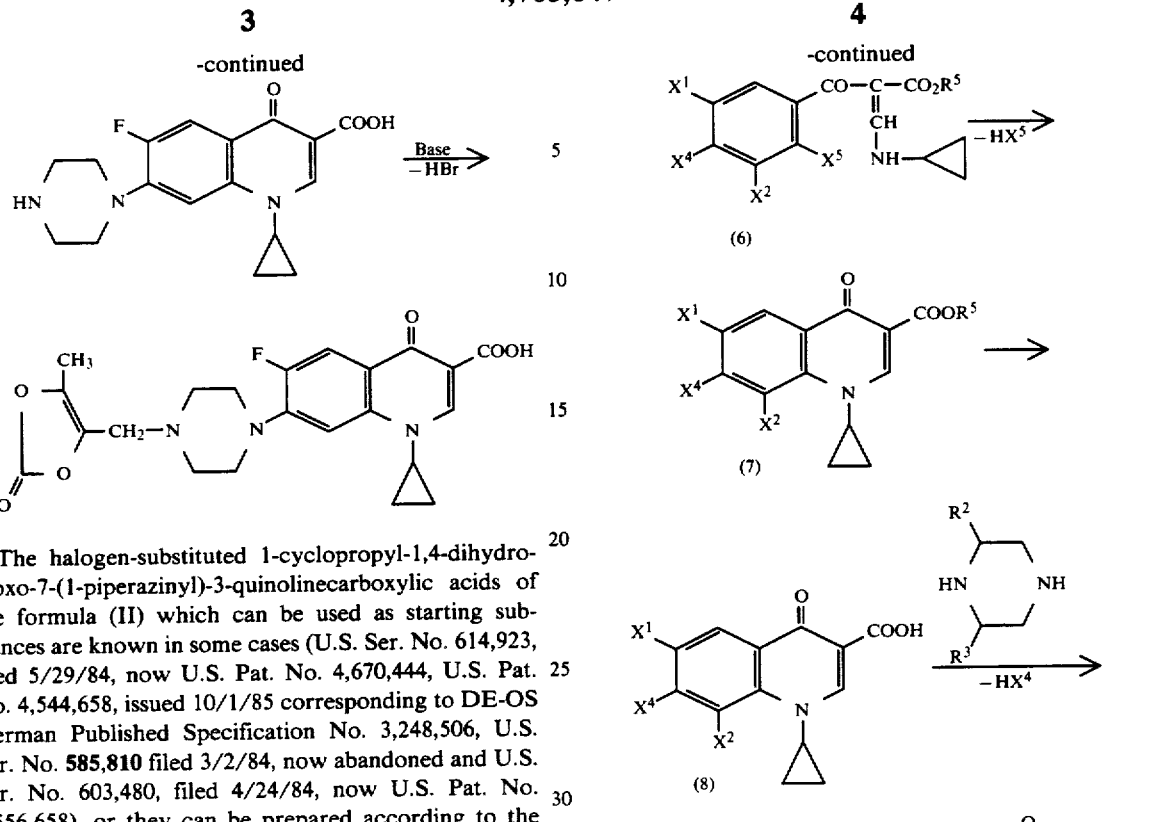

The halogen-substituted 1-cyclopropyl-1,4-dihydro-4-oxo-7-(1-piperazinyl)-3-quinolinecarboxylic acids of the formula (II) which can be used as starting substances are known in some cases (U.S. Ser. No. 614,923, filed 5/29/84, now U.S. Pat. No. 4,670,444, U.S. Pat. No. 4,544,658, issued 10/1/85 corresponding to DE-OS German Published Specification No. 3,248,506, U.S. Ser. No. 585,810 filed 3/2/84, now abandoned and U.S. Ser. No. 603,480, filed 4/24/84, now U.S. Pat. No. 4,556,658), or they can be prepared according to the following equation:

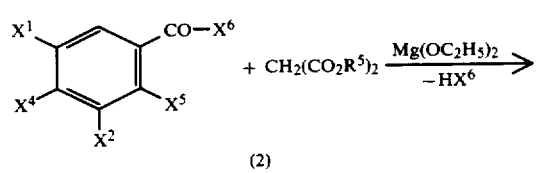

(1)
$X^4, X^5, X^6 =$ F or Cl
$R^5 = CH_3, C_2H_5, C_3H_7$

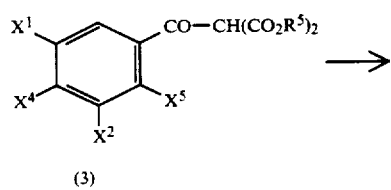

(3)

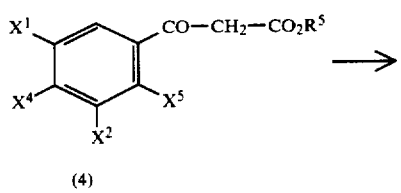

(4)

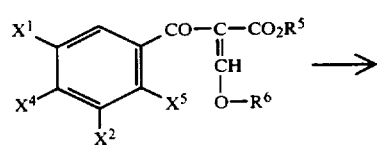

(5)
$R^6 = CH_3, C_2H_5$

According to this reaction, the dialkyl malonate (2) is acylated in the presence of magnesium ethylate with the corresponding benzoyl fluoride or chloride (1) to give the aroylmalonate (3) (Organicum, 3rd edition, 1964, page 438).

Partial hydrolysis ans decarboxylation of (3) in an aqueous medium with catalytic amounts of sulphuric acid or p-toluenesulphonic acid give a good yield of the alkyl aroylacetate (4), which is converted into the corresponding alkyl 2-benzoyl-3-alkoxy-acrylate (5) with trialkyl orthoformate/acetic anhydride. The reaction of (5) with cyclopropylamine in a solvent, such as, for example, methylene chloride, chloroform, methanol, ethanol, cyclohexane or toluene, gives the desired intermediate product (6) in a slightly exothermic reaction.

The cyclization reaction (6)→(7) is carried out in a temperature range from about 60° to 300° C., preferably 80° to 180° C.

Diluents which can be used are dioxane, dimethylsulphoxide, N-methylpyrrolidone, sulpholane, hexamethylphosphoric acid trisamide and, preferably, N,N-dimethylformamide.

Possible acid-binding agents for this reaction stage are potassium tert.-butanolate, butyl-lithium, lithium-phenyl, phenyl-magnesium bromide, sodium methylate, sodium hydride and sodium or potassium carbonate. If hydrogen fluoride is to be split off in this cyclization reaction, potassium fluoride or sodium fluoride is particularly preferably used. It may be beneficial to employ an excess of 10 mol % of base.

The subsequent ester hydrolysis of (7) under basic or acid conditions gives the 1-cyclopropyl-1,4-dihydro-4-oxo-3-quinolinecarboxylic acids (8), which are reacted with piperazine or substituted piperazines in the last step to give the corresponding 1-cyclopropyl-1,4-dihydro-4-oxo-7-(1-piperazinyl)-3-quinolinecarboxylic acids (II).

Some of the benzoyl halides (1) used as starting substances for this synthesis route are new, and they are prepared as follows:

3,5-Dichloro-2,4-difluoro-benzoyl fluoride (boiling point 97° C./20 mbar; $n_D^{20} = 1.5148$) and 5-chloro-2,3,4-trifluorobenzoyl fluoride (boiling point 68°-70°/20 mbar; $n_D^{20} = 1.4764$) are obtained side by side when tetrachlorobenzoyl chloride is heated to elevated temperatures with potassium fluoride in sulpholane:

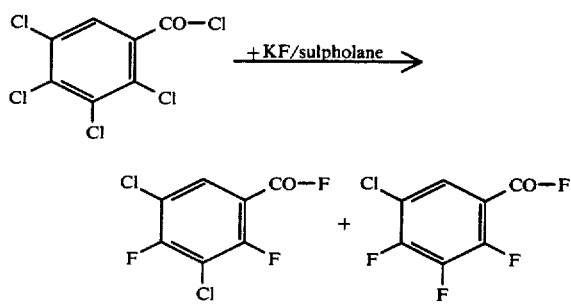

Chlorination of 2,4,5-trifluorobenzoic acid in chlorosulphonic acid gives 3-chloro-2,4,5-trifluorobenzoic acid, which is reacted as the crude product with thionyl chloride to give 3-chloro-2,4,5-trifluorobenzoyl chloride (boiling point 94° C./18 mbar; $n_D^{20} = 1.5164$):

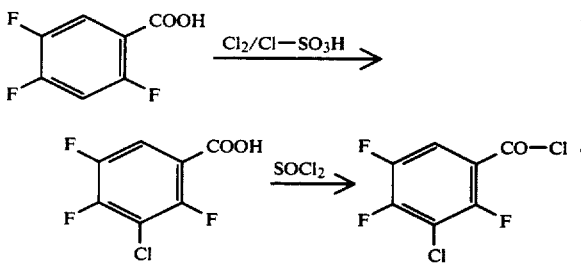

The reactive 1,3-dioxolen-2-ones of the formula (III) which can be used as starting substances are known from the literature, or they can be obtained by processes which are known from the literature: European Patent Applications Nos. 39,086, 39,477, 67,411, 78,413 and 90,344, U.S. Pat. No. 4,434,173 and Japanese Patent Applications Nos. 58 069,875 and 59 025,386. Examples which may be mentioned are: 4-bromomethyl-1,3-dioxol-2-one, 4-bromomethyl-5-methyl-1,3-dioxol-2-one, 4-chloromethyl-5-methyl-1,3-dioxol-2-one, 4-methylsulphonyloxymethyl-1,3-dioxol-2-one, 4-trifluoromethylsulphonyloxymethyl-5-methyl-1,3-dioxol-2-one, 4-bromomethyl-5-tert.-butyl-1,3-dioxol-2-one, 4-bromomethyl-5-phenyl-1,3-dioxol-2-one and 3-bromo-1,2-carbonyldioxy-cyclohexene.

The reaction of II with III is preferably carried out in a diluent, such as dimethylsulphoxide, N,N-dimethylformamide, hexamethylphosphoric acid trisamide, sulpholane, diethylene glycol dimethyl ether or pyridine, in the presence of an acid-binding agent. Mixtures of these solvents can also be used.

Acid-binding agents which can be used are all the customary inorganic acid-binding agents. These include, preferably, the alkali metal hydroxides, alkali metal bicarbonates, alkali metal carbonates, organic amines and amidines. Particularly suitable specific examples which may be mentioned are: sodium hydroxide, potassium hydroxide, sodium bicarbonate, potassium bicarbonate, sodium carbonate, potassium carbonate, triethylamine, 1,4-diaza-bicyclo[2,2,2]-octane (DABCO) or 1,8-diazabicyclo[5,4,0]-undec-7-ene (DBU).

The reaction temperatures can be varied within a substantial range. In general, the reaction is carried out between about −20° and +150° C., preferably between 0° and 40° C.

The reaction can be carried out under normal pressure, but also under increased pressure. It is in general carried out under pressures between about 1 and about 100 bar, preferably between 1 and 10 bar.

In carrying out the process according to the invention, 1 to 3 moles, preferably 1 to 1.5 moles, of the compound (III) are employed per mole of the carboxylic acid (II).

New active compounds which may be mentioned specifically, in addition to the compounds listed in the examples, are: 1-cyclopropyl-6-fluoro-1,4-dihydro-4-oxo-7-[4-(2-oxo-1,3-dioxol-4-yl-methyl)-1-piperazinyl]-3-quinolinecarboxylic acid, 7-[4-(5-tert.-butyl-2-oxo-1,3-dioxol-4-yl-methyl)-1-piperazinyl]-1-cyclopropyl-6-fluoro-1,4-dihydro-4-oxo-3-quinolinecarboxylic acid, 1-cyclopropyl-6-fluoro-1,4-dihydro-4-oxo-7-[4-(2-oxo-5-phenyl-1,3-dioxol-4-yl-methyl)-1-piperazinyl]-3-quinolinecarboxylic acid, 1-cyclopropyl-6-fluoro-1,4-dihydro-4-oxo-7-[4-(4,5,6,7-tetrahydro-2-oxo-1,3-benzdioxol-4-yl)-1-piperazinyl]-3-quinolinecarboxylic acid, 1-cycloporopyl-6,8-difluoro-1,4-dihydro-7-[3,5-dimethyl-4-(5-methyl-2-oxo-1,3-dioxol-4-yl-methyl)-1-piperazinyl]-4-oxo-3-quinolinecarboxylic acid, 1-cyclo propyl-6,8-difluoro-1,4-dihydro-7-[4-(5-methyl-2-oxo-1,3-dioxol-4-yl-methyl)-3-phenyl-1-piperazinyl]-4-oxo-3-quinolinecarboxylic acid and 1-cyclopropyl-6,8-difluoro-1,4-dihydro-7-[4-(5-methyl-2-oxo-1,3-dioxol-4-yl-methyl)-3-(2-thienyl)-1-piperazinyl]-4-oxo-3-quinolinecarboxylic acid.

| Example of a tablet according to the invention | |
|---|---|
| Each tablet contains: | |
| Compound of Example 1 | 583.0 mg |
| Microcrystalline cellulose | 55.0 mg |
| Corn starch | 72.0 mg |
| Insoluble poly-(1-vinyl-2-pyrrolidone) | 30.0 mg |
| Highly disperse silicon dioxide | 5.0 mg |
| Magnesium stearate | 5.0 mg |
| | 750.0 mg |
| The lacquered shell contains: | |
| Poly-(O—hydroxypropyl-O—methyl)-cellulose 15 cp | 6.0 mg |
| Macrogol 4000 rec. INN (polyethylene glycol DAB) | 2.0 mg |
| Titanium(IV) oxide | 2.0 mg |
| | 10.0 mg |

The compounds according to the invention exhibit, in addition to a low toxicity, a broad antibacterial spectrum against Gram-positive and Gram-negative germs, in particular against Enterobacteriaceae; and above all also against those which are resistant towards various antibiotics, such as, for example, penicillins, cephalosporins, aminoglycosides, sulphonamides and tetracyclines.

These useful properties enable them to be used as chemotherapeutic active compounds in medicine and as as substances for the preservation of inorganic and organic materials, in particular of all types of organic materials, for example polymers, lubricants, paints, fibers, leather, paper and wood, and foodstuffs and water.

The compounds according to the invention are active against a very broad spectrum of microorganisms. With their aid it is possible to combat Gram-positive and Gram-negative bacteria and bacteria-like microorganisms and to prevent, alleviate and/or cure the diseases caused by these pathogens.

The compounds according to the invention are particularly active against bacteria and bacteria-like microorganisms. They are therefore particularly suitable, in human medicine and veterinary medicine, for the prophylaxis and chemotherapy of local and systemic infections caused by these pathogens. For example, local and/or systemic diseases caused by the following pathogens or by mixtures of the following pathogens can be treated and/or prevented:

Gram-positive cocci, for example Staphylococci (*Staph. aureus* and *Staph. epidermidis*) and Streptococci (*Strept. agalactiae, Strept. faecalis, Strept. pneumoniae* and *Strept. pyogenes*); Gram-negative cocci (*Neisseria gonorrhoeae*) and Gram-negative rod-shaped bacilli, such as Enterobacteriaceae, for example *Escherichia coli, Haemophilus influenzae,* Citrobacter (*Citrob. freundii* and *Citrob. divernis*), Salmonella and Shigella; and furthermore Klebsiellae (*Klebs. pneumoniae* and *Klebs. oxytoca*), Enterobacter (*Ent. aerogenes* and *Ent. agglomerans*), Hafnia, Serratia (*Serr. marcescens*), Proteus (*Pr. mirabilis, Pr. rettgeri* and *Pr. vulgaris*), Providencia, Yersinia and the genus Acinetobacter. The antibacterial spectrum moreover includes the genus Pseudomonas (*Ps. aeruginosa* and *Ps. maltophilia*) and strictly anaerobic bacteria, such as, for example, *Bacteroides fragilis,* representatives of the genus Peptococcus, Peptostreptococcus and the genus Clostridium; and furthermore Mykoplasma (*M. pneumoniae, M. hominis* and *M. urealyticum*) as well as Mycobacteria, for example Mycobacterium tuberculosis.

The above list of pathogens is purely illustrative and is in no way to be interpreted as restrictive. Examples which may be mentioned of diseases which can be prevented, alleviated and/or cured by the compounds according to the invention are: otitis, pharyngitis; pneumonia, peritonitis; pyelonephritis; cystitis; endocarditis; osteomyelitis; bronchitis; arthritis; local infections; and septic diseases.

The present invention includes pharmaceutical formulations which, in addition to non-toxic, inert pharmaceutically suitable excipients, contain one or more compounds according to the invention or consist of one or more active compounds according to the invention, as well as processes for the preparation of these formulations.

The present invention also includes pharmaceutical formulations in dosage units. This means that the formulations are in the form of individual parts, for example tablets, dragees, capsules, pills, suppositories and ampules, the active compound content of which corresponds to a fraction or a multiple of an individual dose.

The dosage units can contain, for example, 1, 2, 3 or 4 individual doses or ½, ⅓ or ¼ of an individual dose. An individual dose preferably contains the amount of active compound which is given in one administration and which usually corresponds to a whole, a half, one third or one quarter of a daily dose.

By non-toxic, inert pharmaceutically suitable excipients there are to be understood solid, semi-solid or liquid diluents, fillers and formulation auxiliaries of every kind.

Tablets, dragees, capsules, pills, granules, suppositories, solutions, suspensions and emulsions, pastes, ointments, gels, creams, lotions, powders and sprays may be mentioned as preferred pharmaceutical formulations.

Tablets, dragees, capsules, pills and granules can contain the active compound or compounds alongside the customary excipients, such as (a) fillers and extenders, for example starches, lactose, sucrose, glucose, mannitol and silica, (b) binders, for example carboxymethylcellulose, alginates, gelatine and polyvinylpyrrolidone, (c) humectants, for example paraffin and (f) absorption accelerators, for example quaternary ammonium compounds, (g) wetting agents, for example cetyl alcohol and glycerol monostearate, (h) adsorbents, for example kaolin and bentonite, and (i) lubricants, for example talc, calcium stearate, magnesium stearate and solid polyethylene glycols, or mixtures of the substances listed under (a) to (i).

The tablets, dragees, capsules, pills and granules can be provided with the customary coatings and shells, optionally containing opacifying agents, and can also be of such composition that they release the active compound or compounds only, or preferentially, in a cetain part of the intestinal tract, optionally in a delayed manner, examples of embedding compositions which can be used being polymeric substances and waxes.

The active compound or compounds, optionally together with one or more of the abovementioned excipients, can also be in a microencapsulated form.

Suppositories can contain, in addition to the active compound or compounds, the customary water-soluble or water-insoluble excipients, for example polyethylene glycols, fats, for example cacao fat and higher esters (for example $C_{14}$-alcohol with $C_{16}$-fatty acid), or mixtures of these substances.

Ointments, pastes, creams and gels can contain, in addition to the active compound or compounds, the customary excipients, for example animal and vegetable fats, waxes, paraffins, starch, tragacanth, cellulose derivatives, polyethylene glycols, silicones, bentonites, silica, talc and zinc oxide, or mixtures of these substances.

Powders and sprays can contain, in addition to the active compound or compounds, the customary excipients, for example lactose, talc, silica, aluminum hydroxide, calcium silicate and polyamide powder, or mixtures of these substances. Sprays can additionally contain the customary propellants, for example chlorofluorohydrocarbons.

Solutions and emulsions can contain, in addition to the active compound or compounds, the customary excipients, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, corn germ oil, olive oil, castor oil and sesame oil, glycerol, glycerol formal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol or propylene glycol, suspending agents, for example ethoxylated isostearyl alcohols, polyoxyethylene sorbitol esters and sorbitan esters, microcrystalline cellulose, aluminum metahydroxide, bentonite, agar-agar and tragacanth, or mixtures of these substances.

The formulation forms mentioned can also contain colorants, preservatives and additives which improve the odor and flavor, for example peppermint oil and eucalyptus oil, and sweeteners, for example saccharin.

The therapeutically active compounds should preferably be present in the abovementioned pharmaceutical formulations in a concentration of about 0.1 to 99.5, preferably about 0.5 to 95% by weight of the total mixture.

The abovementioned pharmaceutical formulations can also contain other pharmaceutical active compounds in addition to the compounds according to the invention.

The abovementioned pharmaceutical formulations are prepared in the customary manner by known methods, for example by mixing the active compound or compounds with the excipient or excipients.

The active compounds or the pharmaceutical formulations can be administered locally, orally, parenterally, intraperitoneally and/or reactally, preferably orally or parenterally, such as intravenously or intramuscularly.

In general, it has proved advantageous both in human medicine and in veterinary medicine to administer the active compound or compounds according to the invention in total amounts of about 0.5 to about 500, preferably 5 to 100 mg/kg of body weight every 24 hours, if appropriate in the form of several individual doses, in order to achieve the desired results. An individual dose preferably contains the active compound or compounds according to the invention in amounts of about 1 to 250, in particular 3 to 60 mg/kg of body weight. It may, however, be necessary to deviate from the dosages mentioned, and in particular to do so as a function of the nature and body weight of the subject to be treated, the nature and severity of the disease, the nature of the formulation and of the administration of the medicament and the period or interval over which administration takes place.

Thus it can in some cases suffice to manage with less than the abovementioned amount of active compounds, while in other cases the abovementioned amount of active compound must be exceeded. The particular optimum dosage required and the mode of administration of the active compounds can easily be determined by anyone skilled in the art on the basis of his expert knowledge.

The new compounds can be administered in the customary concentrations and formulations, together with the feed or with feed formulations or with the drinking water. Infection by Gram-negative or Gram-positive bacteria can thereby be prevented, alleviated and/or cured, and promotion of growth and an improvement in feed utilization can thereby be achieved.

The MIC values are given in the following table.

TABLE

| MIC values of the compound from Example 1 (agar dilution test/Isosensitest agar) | |
|---|---|
| E. coli Neumann | ≦0.015 |
| Klebsiella 8085 | ≦0.015 |
| Proteus vulgaris 1017 | ≦0.015 |
| Providencia 12012 | 0.03 |
| Serratia 16040 | 8 |
| Staphylococcus FK 422 | 0.25 |
| Streptococcus 27101 | 0.5 |
| Pseudomonas Ellsworth | 0.06 |

PREPARATION OF THE STARTING SUBSTANCES

Example A

6-Chloro-1-cyclopropyl-7,8-difluoro-1,4-dihydro-4-oxo-3-quinolinecarboxylic acid

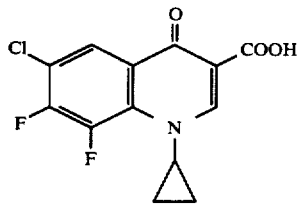

15.7 g (0.65 mole) of magnesium filings are stirred in 40 ml of ethanol and 2 ml of tetrachloromethane and, when the reaction has started, 103 g (0.64 mole) of diethyl malonate in 80 ml of ethanol and 250 ml of toluene are added dropwise at 50°-60° C. The mixture is subsequently stirred at this temperature for 1 hour and cooled to −5° to −10° C., a solution of 138 g (0.65 mole) of 5-chloro-2,3,4-benzoyl fluoride in 63 ml of toluene is added dropwise and the mixture is stirred at 0° for a further hour and left to stand overnight at room temperature. Thereafter, it is warmed at 40°-50° C. for a further 2 hours and cooled and 250 ml of ice-water and 38.5 ml of concentrated sulphuric acid are added. The organic phase is separated off, the aqueous phase is extracted with 2 portions of 150 ml of toluene and the combined organic phases are washed with saturated sodium chloride solution, dried with sodium sulphate and concentrated.

200 ml of water are added to the residue (the addition of 0.4 g of 4-toluenesulphonic acid is advantageous here) and the mixture is heated under reflux for 5 hours to effect de-ethoxycarbonylation. The mixture is extracted with 3 portions of 200 ml of methylene chloride, the organic phase is washed with saturated sodium chloride solution, dried with sodium sulphate and concentrated and the residue is distilled under a high vacuum. 103 g (56.5%) of ethyl (5-chloro-2,3,4-trifluoro-benzoyl)-acetate of boiling point 110° C./0.9 mm Hg are obtained.

103 g (0.37 mole) of the resulting ester and 83 g (0.56 mole) of triethyl orthoformate are heated at 150°-160° C. with 95 g of acetic anhydride for 2 hours and the mixture is subsequently concentrated at 120°-130° C. under normal pressure and then under a high vacuum. 115 g (92% of theory) and ethyl 2-(5-chloro-2,3,4-trifluoro-benzoyl)-3-ethoxyacrylate are obtained as an oil.

14.8 g (0.26 mole) of cyclopropylamine are added dropwise to 84.1 g (0.25 mole) of this compound in 170 ml of ethanol, while cooling with ice, and the mixture is stirred at room temperature for 2 hours. It is then stirred with 170 ml of water and cooled in ice and the precipitate which has separated out is filtered off with suction, washed with water and a little methanol and dried. 47 g (54%) of ethyl 2-(5-chloro-2,3,4-trifluoro-benzoyl)-3-cyclopropylamino-acrylate of melting point 71°–73° C. are obtained. According to the ¹H-NMR spectrum, a cis/trans mixture is present.

47 g (0.14 mole) of this compound are heated at 160°–170° C. in 230 ml of dimethylformamide with 9.7 g (0.23 mole) of sodium fluoride for 2 hours. The reaction mixture is poured into 400 ml of ice-water and the precipitate is filtered off with suction, washed with water and dried. 44 g (99%) of ethyl 6-chloro-1-cyclopropyl-7,8-difluoro-1,4-dihydro-4-oxo-3-quinolinecarboxylate of melting point 169°–172° C. are isolated.

33 ml of concentrated sulphuric acid are added to 44 g (0.13 mole) of the quinolinecarboxylate in 300 ml of glacial acetic acid and 179 ml of water and the reaction mixture is heated at 150° C. for 2 hours. It is stirred into 400 ml of ice-water and the precipitate is filtered off with suction, washed with water and dried. 37 g (95% of theory) of 6-chloro-1-cyclopropyl-7,8-difluoro-1,4-dihydro-4-oxo-3-quinolinecarboxylic acid of melting point 200°–204° C. are isolated.

Example B

8-Chloro-1-cyclopropyl-6,7-difluoro-1,4-dihydro-4-oxo-3-quinolinecarboxylic acid

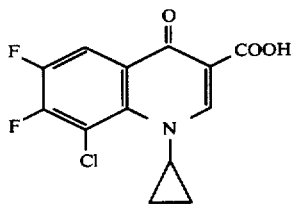

3-Chloro-2,4,5-trifluoro-benzoyl chloride is reacted analogously to Example A, the reaction passing through the following stages: ethyl(3-chloro-2,4,5-trifluoro-benzoyl)-acetate as the enol (yield: 42%, melting point 72°–75° C.), ethyl 2-(3-chloro-2,4,5-trifluoro-benzoyl)-3-ethoxy-acrylate (crude yield: 95%, oil), ethyl 2-(3-chloro-2,4,5-trifluoro-benzoyl-3-cyclopropylamino-acrylate (yield: 67%, melting point 78°–80° C.), ethyl 8-chloro-1-cyclopropyl-6,7-difluoro-1,4-dihydro-4-oxo-3-quinolinecarboxylate (yield: 85%, melting point 154°–157° C.), chloro-1-cyclopropyl-6,7-difluoro-1,4-dihydro-4-oxo-3-quinolinecarboxylic acid (yield: 97.6%, melting point 189°–192° C.).

Example C 6,8-Dichloro-1-cyclopropyl-7-fluoro-1,4-dihydro-4-oxo-3-quinolinecarboxylic acid

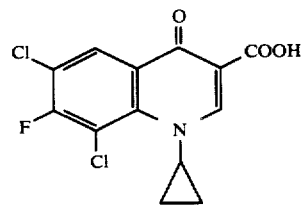

3,5-Dichloro-2,4-difluoro-benzoyl fluoride is reacted analogously to Example A, the reaction passing through the following stages: ethyl(3,5-dichloro-2,4-difluoro-benzoyl)-acetate (yield: 43%, boiling point 133° C./2.5 mm Hg), ethyl 2-(3,5-dichloro-2,4-difluoro-benzoyl)-3-ethoxy-acrylate (crude yield: 91%, oil), ethyl 2-(3,5-dichloro-2,4-difluoro-benzoyl)-3-cyclopropylamino-acrylate (yield: 96%, melting point 71°–74° C.), ethyl 6,8-dichloro-1-cyclopropyl-7-fluoro-1,4-dihydro-4-oxo-3-quinolinecarboxylate (yield: 97%, melting point 215°–217° C., with decomposition) and 6,8-dichloro-1-cyclopropyl-7-fluoro-1,4-dihydro-4-oxo-3-quinolinecarboxylic acid (yield: 93%; melting point 204°–206° C.).

Example A1

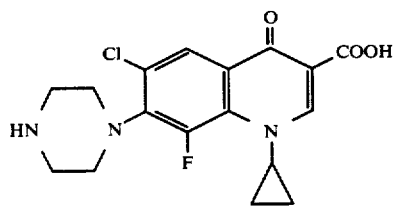

12 g (40 mmoles) of the product from Example A are heated under reflux in 100 ml of pyridine with 17.2 g (0.2 mole) of piperazine for 5 hours. The mixture is concentrated in vacuo, the residue is stirred with 120 ml of water and the mixture is brought to 5 with 2N hydrochloric acid. The precipitate is filtered off with suction, washed with methanol and water, boiled up in 80 ml of methanol and dried. 12.3 g (84% of theory) of 6-chloro-1-cyclopropyl-8-fluoro-1,4-dihydro-4-oxo-7-(1-piperazinyl)-3-quinolinecarboxylic acid of melting point 295°–298° C. (with decomposition) are obtained.

The following 6-chloro-1-cyclopropyl-8-fluoro-1,4-dihydro-4-oxo-3-quinolinecarboxylic acids substituted in the 7-position are obtained analogously to Example A1:

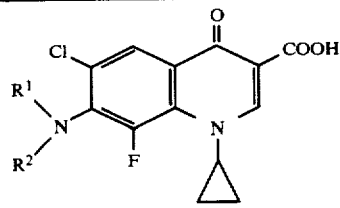

| Example | R¹\N—/R² | Melting point |
|---|---|---|
| A2 | HN⟩N— with CH₃ | 258–282° C. (decomposition) |
| A3 | HN⟩N— with C₂H₅ | 191–195° C. (decomposition) |

-continued

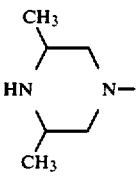

| Example | R¹\N—\R² | Melting point |
|---|---|---|
| A4 | 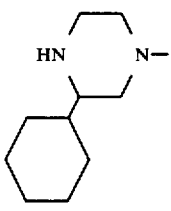 | 255–261° C. (decomposition) |
| A5 | 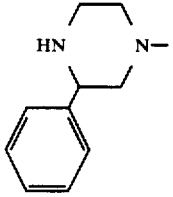 | from ~ 190° C. (decomposition) |
| A6 | 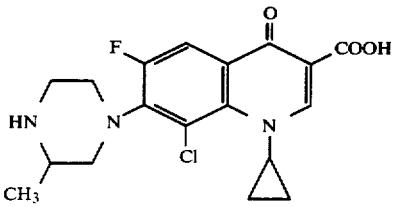 | 154–158° C. |

Example B1

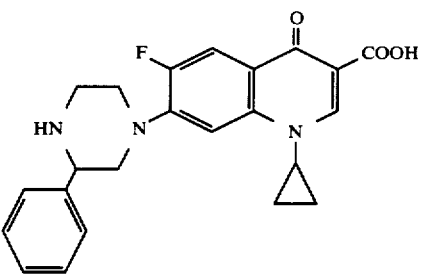

3 g (0.01 mole) of the product from Example B are heated under reflux in 25 ml of pyridine with 4 g (0.04 mole) of 2-methyl-piperazine for 5 hours. The mixture is concentrated in vacuo, 20 ml of water are added, the pH is brought to 5 with 2N hydrochloric acid and the precipitate which separates out is recrystallized from methanol. 0.6 g (16% of theory) of 8-chloro-1-cyclopropyl-6-fluoro-1,4-dihydro-7-(3-methyl-1-piperazinyl)-4-oxo-3-quinolinecarboxylic acid of melting point 318°–325° C. (with decomposition) is obtained.

Example B2

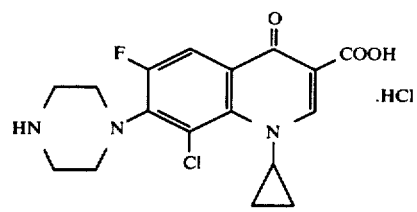

The product from Example B is reacted with piperazine under reflux for 1.5 hours analogously to Example B1 and the reaction mixture is treated with hydrochloric acid, 8-chloro-1-cyclopropyl-6-fluoro-1,4-dihydro-7-(1-piperazinyl)-3-quinolinecarboxylic acid hydrochloride with a decomposition point above 330° C. being obtained.

Example C1

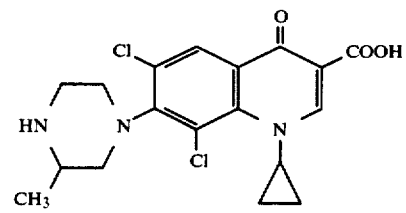

The product from Example C is reacted with 2-methyl-piperazine analogously to Example B1 to give 6,8-dichloro-1cyclopropyl-1,4-dihydro-7-(3-methyl-1-piperazinyl)-4-oxo-3-quinolinecarboxylic acid of melting point 288°–291° C. (with decomposition).

Example D1

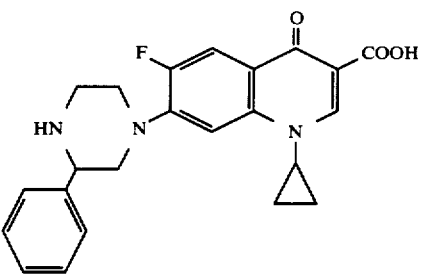

A mixture of 2.8 g (0.01 mole) of 7-chloro-1-cyclopropyl-6-fluoro-1,4-dihydro-4-oxo-3-quinolinecarboxylic acid (U.S. Ser. No. 614,923, filed 5/29/84, now U.S. Pat. No. 4,670,444), 1.8 g (0.011 mole) of 2-phenyl-piperazine and 2.2 g (0.02 mole) of 1,4-diazabicyclo[2,2,-2]octane in 6 ml of dimethylsulphoxide is heated at 140° C. for 4 hours. The solution is concentrated under a high vacuum, the residue is stirred with 20 ml of water and the pH is brought to 7 with 2N hydrochloric acid. The precipitate is filtered off with suction, washed with water and methanol and boiled up in 30 ml of methanol. 1.3 g (32% of theory) of 1-cyclopropyl-6-fluoro-1,4-dihydro-4-oxo-7-(3-phenyl-1-piperazinyl)-3-quinolinecarboxylic acid of melting point 218°–220° C. (with decomposition) (recrystallized from glycol monomethyl ether) are obtained.

The following compounds are obtained analogously to Example D1 using the corresponding piperazines:

| Example | R | Melting point (with decomposition) |
|---|---|---|
| D2 | 4-F-C₆H₄– | 198–203° C. |
| D3 | 4-Cl-C₆H₄– | 207–209° C. (from Methanol) |
| D4 | 4-Br-C₆H₄– | 252–255° C. |
| D5 | 4-CH₃O-C₆H₄– | 208–211° C. (from Ethanol) |
| D6 | 4-(C₆H₅CH₂O)-C₆H₄– | 208–211° C. (from Methanol) |
| D7 | 2,4,5-tri-methoxy/methyl-C₆H₂– | 233–237° C. (from Glycol monomethylether) |
| D8 | 4-(piperidin-1-yl)-C₆H₄– | 156–161° C. |
| D9 | 4-CH₃-C₆H₄– | 258–261° C. |
| D10 | 4-biphenyl– | 278–281° C. |
| D11 | 3-NO₂-C₆H₄– | 247–250° C. (from Methanol) |
| D12 | 2-thienyl– | 218–222° C. (from Acetonitrile) |
| D13 | cyclohexyl– .HCl | 316–320° C. (from Methanol) |

Example D14

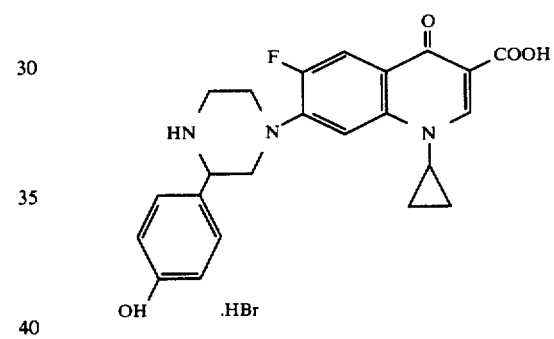

60 ml of 48% strength hydrobromic acid are added to 2.5 g (4.9 mmoles) of the product from Example D6 in 30 ml of ethanol and the mixture is stirred at 55° for 1 hour. The mixture is concentrated in vacuo, 50 ml of water are added to the residue and the precipitate is filtered off with suction and washed with methanol. 1.5 g (66% of theory) of 1-cyclopropyl-6-fluoro-1,4-dihydro-7-[3-(4-hydroxy-phenyl)-1-piperazinyl]-4-oxo-3-quinolinecarboxylic acid hydrobromide of melting point 295°–298° C. (with decomposition) are obtained.

PREPARATION OF THE ACTIVE COMPOUNDS

Example 1

1-Cyclopropyl-6-fluoro-1,4-dihydro-7-[4-(5-methyl-2-oxo-1,3-dioxol-4-yl-methyl)-1-piperazinyl]-4-oxo-3-quinolinecarboxylic acid

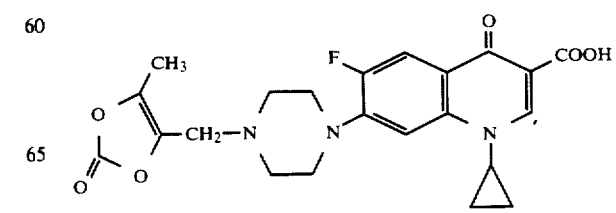

1.15 g (3.5 mmoles) of 1-cyclopropyl-6-fluoro-1,4-dihydro-4-oxo-7-(1-piperazinyl)-3-quinolinecarboxylic acid are stirred in 20 ml of dimethylformamide with 0.85 g (4.4 mmoles) of 4-bromomethyl-5-methyl-1,3-dioxol-2-one and 0.42 g (4.2 mmoles) of powdered potassium bicarbonate for 3 days, while cooling with ice. The mixture is concentrated in vacuo, the residue is stirred with 20 ml of water, the resulting greasy product is dissolved in methanol and the solution is filtered. The filtrate is left to stand at room temperature for 2 days and the colorless crystals which have precipitated are isolated.

Yield: 0.3 g, melting point: 228°–232° C. (with decomposition).

The following compounds are prepared in accordance with Example 1:

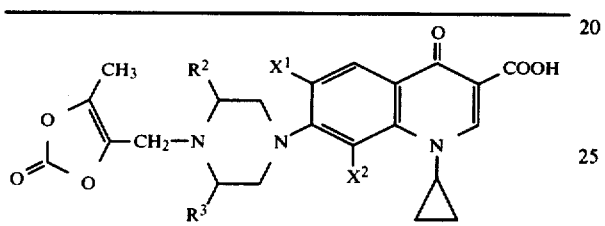

| Example | $R^2$ | $R^3$ | $X^1$ | $X^2$ |
|---|---|---|---|---|
| 2 | H | H | Cl | F |
| 3 | CH₃ | H | Cl | F |
| 4 | CH₃ | CH₃ | Cl | F |
| 5 | cyclohexyl | | H | Cl | F |
| 6 | phenyl | | H | Cl | F |
| 7 | H | H | H | F | Cl |
| 8 | CH₃ | H | F | Cl |
| 9 | CH₃ | H | Cl | Cl |
| 10 | CH₃ | H | F | H |
| 11 | CH₃ | CH₃ | F | H |
| 12 | 4-F-phenyl | | H | F | H |
| 13 | 4-Cl-phenyl | | H | F | H |
| 14 | 4-Br-phenyl | | H | F | H |
| 15 | 4-OCH₃-phenyl | | H | F | H |

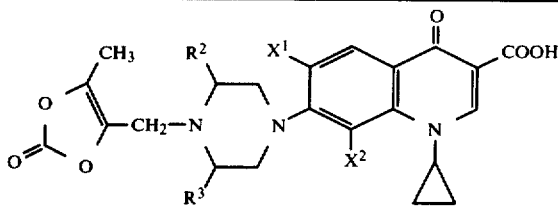

| Example | $R^2$ | $R^3$ | $X^1$ | $X^2$ |
|---|---|---|---|---|
| 16 | 4-OH-phenyl | | H | F | H |
| 17 | 4-CH₃-phenyl | | H | F | H |
| 18 | 4-piperidino-phenyl | | H | F | H |
| 19 | 2-thienyl | | H | F | H |
| 20 | H | H | F | F |
| 21 | CH₃ | H | F | F |

It will be understood that the specification and examples are illustrative but not limitative of the present invention and that other embodiments within the spirit and scope of the invention will suggest themselves to those skilled in the art.

We claim:

1. A 1-cyclopropyl-1,4-dihydro-4-oxo-7-[4-(2-oxo-1,3-dioxol-4-yl-methyl)-1-piperazinyl]-3-quinolinecarboxylic acid of the formula

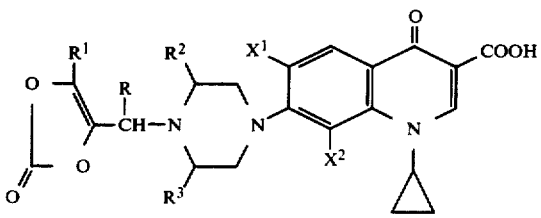

in which

R is hydrogen or, together with $R^1$, forms an alkylene radical with 2 or 3 carbon atoms, $R^1$ is hydrogen, alkyl with 1 to 4 carbon atoms or phenyl, $R^2$ and $R^3$ each independently is hydrogen, methyl, ethyl, cyclohexyl, methylene-dioxyphenyl, furyl, tetrahydrofuryl or thienyl; or phenyl which is optionally mono-, di or tri-substituted by fluorine, chlorine, bromine, methyl, phenyl, cyano, hydroxyl, methoxy, benzyloxy, amino, methylamino, dimethylamino, piperidino or nitro, $X^1$ is hydrogen, halogen, or nitro, and $X^2$ is hydrogen or halogen, or a pharmaceutically acceptable hydrate, acid addition salt, alkali metal salt or alkaline earth metal salt thereof.

2. A compound, hydrate or salt according to claim 1, in which

R is hydrogen,

R¹ is methyl or tert.-butyl, and

R² and R³ each independently is hydrogen, methyl, ethyl, cyclohexyl, thienyl, or phenyl which is optionally mono-, di or tri-substituted by fluorine, chlorine, bromine, methyl, phenyl, cyano, hydroxyl, methoxy, amino, piperidino or nitro.

3. A compound, hydrate or salt according to claim 1, in which

R is hydrogen,

R¹ is methyl,

R² and R³ each independently is hydrogen, methyl, cyclohexyl, thienyl, or phenyl which is optionally mono- or di-substituted by fluorine, chlorine, bromine, methyl, hydroxyl, methoxy, benzyloxy, amino, piperidino or nitro, and X¹ is halogen.

4. A compound according to claim 1, wherein such compound is 1-cyclopropyl-6-fluoro-1,4-dihydro-7-[4-(5-methyl-2-oxo-1,3-dioxol-4-yl-methyl)-1-piperazinyl]-4-oxo-3-quinolinecarboxylic acid of the formula

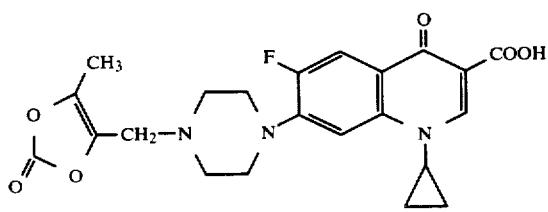

or a pharmaceutically acceptable hydrate, acid addition salt, alkali metal salt or alkaline earth metal salt thereof.

5. A compound according to claim 1, wherein such compound is 8-chloro-1-cyclopropyl-6-fluoro-1,4-dihydro-7-[4-(5-methyl-2-oxo-1,3-dioxol-4-yl-methyl)-1-piperazinyl]-4-oxo-3-quinolinecarboxylic acid of the formula

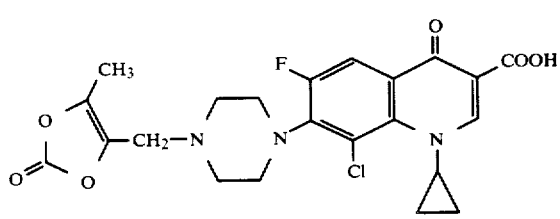

or a pharmaceutically acceptable hydrate, acid addition salt, alkali metal salt or alkaline earth metal salt thereof.

6. A compound according to claim 1, wherein such compound is 8-chloro-1-cyclopropyl-6-fluoro-1,4-dihydro-7-[3-methyl-4-(5-methyl-2-oxo-1,3-dioxol-4-yl-methyl)-1-piperazinyl]-4-oxo-3-quinolinecarboxylic acid of the formula

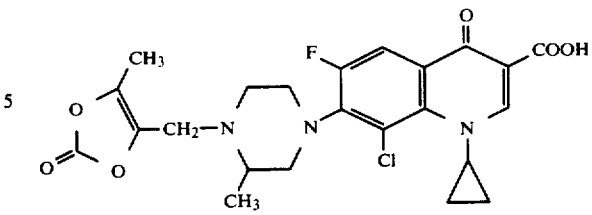

or a pharmaceutically acceptable hydrate, acid addition salt, alkali metal salt or alkaline earth metal salt thereof.

7. A compound according to claim 1, wherein such compound is 1-cyclopropyl-6,8-difluoro-1,4-dihydro-7-[4-(5-methyl-2-oxo-1,3-dioxol-4-yl-methyl)-1-piperazinyl]-4-oxo-3-quinolinecarboxylic acid of the formula

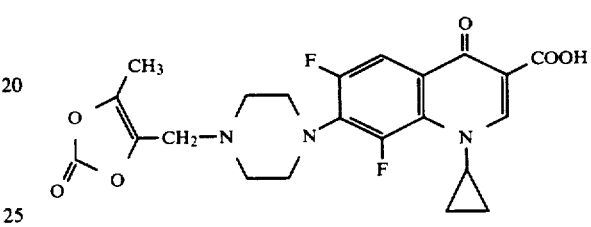

or a pharmaceutically acceptable hydrate, acid addition salt, alkali metal salt or alkaline earth metal salt thereof.

8. A compound according to claim 1, wherein such compound is 8-chloro-1-cyclopropyl-6-fluoro-1,4-dihydro-7-[3,5-dimethyl-4-(5-methyl-2-oxo-1,3-dioxol-4-yl-methyl)-1-piperazinyl]-4-oxo-3-quinolinecarboxylic acid of the formula

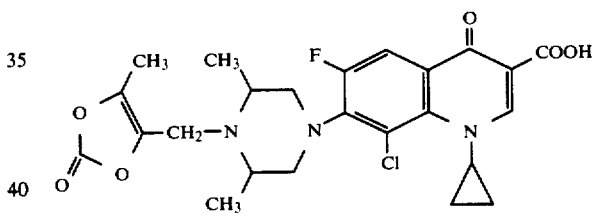

or a pharmaceutically acceptable hydrate, acid addition salt, alkali metal salt or alkaline earth metal salt thereof.

9. An antibacterially active composition comprising an antibacterially effective amount of a compound, hydrate or salt according to claim 1 in admixture with a diluent.

10. A unit dose of a composition according to claim 9 in the form of a tablet, capsule or ampule.

11. A method of combating bacteria which comprises administering to such bacteria, to a habitat thereof or to a patient infected therewith or to be protected therefrom an antibacterially effective amuount of a compound, hydrate or salt according to claim 1.

12. The method according to claim 11, wherein such compound is 8-chloro-1-cyclopropyl-6-fluoro-1,4-dihydro-7-[4-(5-methyl-2-oxo-1,3-dioxol-4-yl-methyl)-1-piperazinyl]-4-oxo-3-quinolinecarboxylic acid, 8-chloro-1-cyclopropyl-6-fluoro-1,4-dihydro-7-[3-methyl-4-(5-methyl-2-oxo-1,3-dioxol-4-yl-methyl)-1-piperazinyl]-4-oxo-3-quinolinecarboxylic acid, 1-cyclopropyl-6,8-difluoro-1,4-dihydro-7-[4-(5-methyl-2-oxo-1,3-dioxol-4-yl-methyl)-1-piperazinyl]-4-oxo-3-quinolinecarboxylic acid or 8-chloro-1-cyclopropyl-6-fluoro-1,4-dihydro-7-[3,5-dimethyl-4-(5-methyl-2-oxo-1,3-dioxol-4-yl-methyl)-1-piperazinyl]-4-oxo-3-quinolinecarboxylic acid or a pharmaceutically acceptable hydrate or salt thereof.

* * * * *

UNITED STATES PATENT AND TRADEMARK OFFICE
CERTIFICATE OF CORRECTION

PATENT NO. : 4,703,047
DATED : October 27, 1987
INVENTOR(S) : Uwe Petersen, et al.

It is certified that error appears in the above-identified patent and that said Letters Patent is hereby corrected as shown below:

| | |
|---|---|
| Title Page, "Abstract" | Line 3 after formula delete "atom" and substitute --atoms--; |
| | Line 5 after formula correct spelling of --dioxyphenyl--; |
| | Line 8 after formula delete "ethoxy" and substitute --methoxy--. |
| Col. 4, line 47 | Delete "ans" and substitute --and-- |
| Col. 6, line 5 | After "inorganic" insert --and organic-- |
| Col. 6, line 40 | Correct spelling of --cyclopropyl-- |
| Col. 6, line 42 | End of line, after "cyclo" insert -- - -- |
| Col. 9, line 54 | Delete "compounds" and substitute --compound-- |
| Col. 14, line 35 | After "dichloro-1" insert -- - -- |

Signed and Sealed this

Fourteenth Day of June, 1988

Attest:

DONALD J. QUIGG

Attesting Officer

Commissioner of Patents and Trademarks